United States Patent
Leute et al.

(10) Patent No.: US 9,120,729 B2
(45) Date of Patent: Sep. 1, 2015

(54) METHOD FOR PURIFYING L-CYSTEINE

(75) Inventors: Maria Leute, Munich (DE); Andreas Boehm, Munich (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/110,755

(22) PCT Filed: Apr. 19, 2012

(86) PCT No.: PCT/EP2012/057109
§ 371 (c)(1),
(2), (4) Date: Oct. 9, 2013

(87) PCT Pub. No.: WO2012/143412
PCT Pub. Date: Oct. 26, 2012

(65) Prior Publication Data
US 2014/0031586 A1    Jan. 30, 2014

(30) Foreign Application Priority Data
Apr. 20, 2011    (DE) .......................... 10 2011 007 790

(51) Int. Cl.
*C07C 227/00* (2006.01)
*C07C 319/28* (2006.01)

(52) U.S. Cl.
CPC .................................... *C07C 319/28* (2013.01)

(58) Field of Classification Search
CPC ............................ C07C 319/28; C07C 323/58
USPC ....................................................... 562/554
See application file for complete search history.

(56) References Cited

U.S. PATENT DOCUMENTS

| | | | |
|---|---|---|---|
| 2,590,209 A | 3/1952 | Roberts | |
| 5,972,663 A | 10/1999 | Winterhalter et al. | |
| 6,372,912 B1 | 4/2002 | Döring et al. | |
| 8,088,949 B2 * | 1/2012 | Boehm | ......................... 562/554 |
| 2008/0190854 A1 | 8/2008 | Boehm | |

FOREIGN PATENT DOCUMENTS

| | | | |
|---|---|---|---|
| EP | 0296937 | * | 12/1988 |
| EP | 1059288 B1 | | 7/2002 |
| EP | 0885962 B1 | | 4/2005 |
| EP | 1958933 A1 | | 8/2008 |

OTHER PUBLICATIONS

Machine translation of description EP0296937 Dec. 1988.*
Machine translation of claims EP0296937 Dec. 1988.*
De Dardel et al., Ion Exchangers, Ullmann's Encyclopedia of Industrial Chemistry, 2008, vol. A14, Chapter 2 (Structures of Ion-Exchange Resins), Wiley-VCH Verlag GmbH & Co. KGaA.
International Search Report for PCT/EP2012/057109 dated Jul. 20, 2012.

* cited by examiner

*Primary Examiner* — Yevegeny Valenrod
*Assistant Examiner* — Blaine G Doletski
(74) *Attorney, Agent, or Firm* — Caesar Rivise, PC

(57) ABSTRACT

The invention relates to a method for producing a purified solution containing L-cysteine from a fermentation broth containing L-cysteine. In said method, the fermentation broth containing L-cysteine, at a pH value from pH 6 to 9, is brought in contact with a basic anion exchanger, wherein the L-cysteine bonds to the anion exchanger. The anion exchanger is then rinsed with a first washing solution, and the bonded L-cysteine is removed from the anion exchanger by means of an acid and transferred into an eluate. Said eluate, having a pH≤4, is brought in contact with an acidic cation exchanger, wherein the L-cysteine bonds to the cation exchanger. The cation exchanger is rinsed with a second washing solution, and the bonded L-cysteine is removed from the cation exchanger by means of a strong acid.

14 Claims, No Drawings

METHOD FOR PURIFYING L-CYSTEINE

BACKGROUND OF THE INVENTION

The invention relates to a method for purifying L-cysteine from an L-cysteine-containing fermentation broth.

L-Cysteine is an amino acid which, owing to the good solubility in water and the high sensitivity of the SH group to many reagents, e.g. to oxidants, can be purified and isolated only with great difficulty and with a high outlay.

U.S. Pat. No. 2,590,209 describes a general process for separating amino acid mixtures into acidic, neutral and basic amino acids, in which an acidic protein hydrolysate is firstly passed over a cation exchanger, the acidic and neutral amino acids are then eluted by means of ammonium hydroxide, while the basic amino acids are retained. These are subsequently flushed from the cation exchanger using a carbonate solution. The acidic and neutral amino acids are in turn separated by means of a downstream anion exchanger on which only the acidic amino acids are bound. The process described is not suitable for purifying cysteine since bases are used as eluent but cysteine is particularly oxidation-sensitive at high pH values.

Problems in the purification and also the prior art for isolation of L-cysteine are described in EP 1958933 A1 (corresponds to US 2008-0190854). This application describes a process in which an L-cysteine-containing fermentation broth comprising an oxidant which is able to oxidize L-cysteine at pH values of <5 is brought into contact at a pH of from 5 to 9 with an ion exchanger, where a pH of <5, preferably pH<2, occurs in the fermentation broth. Here, the L-cysteine binds to the ion exchanger and the bound L-cysteine is removed by means of an eluent from the ion exchanger. L-Cysteine monohydrochloride monohydrate can subsequently be obtained from the eluate by fractional crystallization. Chlorides of inorganic alkali metal and alkaline earth metal ions and also ammonium chloride are firstly crystallized by addition of concentrated HCl or by introduction of HCl gas. After filtration, the L-cysteine-containing mother liquor is cooled to −10° C. and L-cysteine hydrochloride monohydrate crystallizes. However, yield and purity are dependent on the purity of the L-cysteine-containing solution used; purities of up to >98% by weight require further fractional crystallization and/or recrystallization.

Processes for the fermentative preparation of L-cysteine are known, for example, from EP0885962B1 (corresponds to U.S. Pat. No. 5,972,663A). The processes allow inexpensive access to fermentation broths containing large amounts of L-cysteine.

Such an L-cysteine-containing fermentation broth is a complex mixture of substances. It contains not only L-cysteine but generally also L-cystine which is easily formed from L-cysteine under the conditions of fermentation, in particular by oxidation by means of oxygen present. In the presence of aldehydes or ketones, corresponding hemithioketals and/or thiazolidine derivatives of L-cysteine can also be present, as described, for example, in EP0885962B1. The fermentation broths can also contain small amounts of further amino acids or derivatives thereof. They generally also contain carbohydrates, salts of organic and inorganic cations and anions, e.g. alkali metal and alkaline earth metal salts and also traces of heavy metal salts (e.g. Fe, Cu, Mn, Zn, etc.), colorants and further impurities and additives, e.g. undesirable metabolites of the microorganisms used in the fermentation. Furthermore, the fermentation broths can also contain the raw materials and constituents used in the fermentation, e.g. customary C sources such as glucose, lactose, starch and the like, N sources such as ammonia/ammonium or proteins or protein hydrolysates and the like and also S sources such as sulfide, sulfite, sulfate, thiosulfate or dithionite and the like. Since L-cysteine is a sulfur-containing amino acid, an S source such as sulfide, sulfite, sulfate, thiosulfate or dithionite is generally fed in during the fermentation in order to provide a sufficient amount of the sulfur required for the formation of L-cysteine. Furthermore, dissolved oxygen is also present in the fermentation broths as a result of the oxygen introduced during the fermentation. The pH of these fermentation broths is usually 7, as described, for example, in EP0885962B1. Apart from the complexity of the composition of the fermentation broth, natural fluctuations in the ratio of the individual constituents additionally occur since the broth is a product of biological processes.

DESCRIPTION OF THE INVENTION

It is an object of the present invention to provide a simple, inexpensive and industrially implementable process for producing a purified L-cysteine-containing solution from an L-cysteine-containing fermentation broth.

This object is achieved by a process in which an L-cysteine-containing fermentation broth is brought into contact at a pH of from 6 to 9 with a basic anion exchanger, where the L-cysteine binds to the anion exchanger, the anion exchanger is flushed with a first washing solution, the bound L-cysteine is removed from the anion exchanger by means of an acid and transferred into an eluate and the eluate is brought into contact at a pH of ≤4 with an acidic cation exchanger, where the L-cysteine binds to the cation exchanger, the cation exchanger is flushed with a second washing solution and the bound L-cysteine is removed from the cation exchanger by means of a strong acid.

The process of the invention always gives a uniform solution regardless of fluctuations in the composition of the fermentation broth since L-cysteine is separated off reliably and virtually completely from all accompanying substances. If required, L-cysteine, L-cysteine hydrochloride or L-cysteine hydrochloride monohydrate can then be obtained as solid from the solution. For this purpose, the solution obtained is preferably concentrated until the desired product, preferably L-cysteine hydrochloride monohydrate, crystallizes out. The L-cysteine hydrochloride monohydrate obtained in this way has a purity of >98% by weight. A fractional crystallization as described in EP1958933A1 is not necessary.

An L-cysteine-containing fermentation broth is, preferably after the cells and solids have been separated off, purified using the process of the invention firstly by means of a basic ion exchanger and subsequently by means of an acidic ion exchanger.

Acidic and basic ion exchangers are known and commercially available. A selection of various suitable materials is reported in Ullmann's Encyclopedia of Industrial Chemistry, Vol. A14, p. 451. As active ion-exchanging groups, they contain, for example, carboxylic acid groups (weakly acidic ion exchangers), sulfonic acid and phosphonic acid groups (strongly acidic ion exchangers), quaternary ammonium groups (strongly basic ion exchangers) or amine groups (weakly basic ion exchangers). As counterions to the active ion-exchanging groups, cations or anions can be bound to the ion exchanger. Acidic ion exchangers are frequently used in the protonated $H^+$ form but further customary counterions are, for example, also ammonium ions, alkali metal ions and/or alkaline earth metal ions. Basic, in particular strongly basic, ion exchangers are frequently used in the $OH^-$ form, but further customary counterions are, for example, also chloride and further anions described in the prior art.

Preference is given to using strongly acidic and strongly basic ion exchangers. The anion exchanger is preferably used in the OH⁻ form, while the cation exchanger is preferably used in the H⁺ form. However, it is in principle also possible to use ion exchangers having other counterions.

The L-cysteine-containing fermentation broth is preferably firstly brought into contact with a strongly basic anion exchanger and the L-cysteine-containing eluate from the anion exchanger is subsequently brought into contact with a strongly acidic cation exchanger. This can be effected, for example, by the fermentation broth or eluate being pumped through columns packed with the corresponding ion exchangers. The pH of the fermentation broth applied corresponds to the pH during the fermentation and is in a pH range of 6-9 and preferably at a pH of 6-8.

The L-cysteine-containing eluate from the anion exchanger is preferably applied with a pH of from 1 to 4 to the cation exchanger.

The first washing solution is preferably water having a pH in the range from 6 to 8, particularly preferably water having a pH of 7 (neutral water). Washing with this washing solution removes neutral and cationic constituents of the fermentation broth from the anion exchanger.

The second washing solution is preferably water having a pH in the range from 4 to 8, particularly preferably water having a pH in the range from 5 to 7. Washing with the neutral to slightly acidic water removes anionic impurities from the cation exchanger.

All pH values reported in the context of the present patent application relate to a determination of the pH at 25° C.

In the experiments which led to the present invention, it was surprisingly found that L-cysteine, which is easily converted at pH values of >7 into L-cystine by means of atmospheric oxygen or other oxidants, can be absorbed on a basic ion exchanger and eluted from this again without appreciable oxidation. This was particularly surprising because significant oxidation of L-cysteine to L-cystine is observed when a base, e.g. aqueous ammonia, is used in the elution of L-cysteine bound to an acidic cation exchanger. This oxidation results in a direct, significant decrease in yield (see examples 3 and 6), and the economics of the process are therefore no longer satisfactory.

If a neutral L-cysteine-containing solution or fermentation broth is brought into contact with an anion exchanger, preferably a strongly basic anion exchanger in the OH⁻ form, L-cysteine is bound virtually quantitatively to the anion exchanger in this operation. Other amino acids, e.g. L-cystine, and/or further anions which may be present in the fermentation broth can also be bound to the ion-exchange resin here. Many further impurities, e.g. neutral compounds or cations or their corresponding bases, do not bind to the anion-exchange resin and are present in the outflow.

After elution using an acid, the L-cysteine-containing solution is brought into contact with a cation exchanger, preferably a strongly acidic cation exchanger in the H⁺ form, resulting in L-cysteine being bound quantitatively to the cation exchanger. Anionic impurities still present do not bind to the cation exchange resin and are present in the outflow.

As eluent, preference is given to using strong acids, which for the present purposes are preferably acids having a pKa of less than 4.5, and particularly preferably hydrochloric acid. Aqueous hydrochloric acid is particularly useful.

In elution using hydrochloric acid, aqueous hydrochloric acid, preferably of different normalities, more preferably 0.01-12N HCl and particularly preferably 0.01-1N HCl, is pumped through the anion exchanger loaded with L-cysteine. Very particular preference is given to an eluent in which the HCl concentration is increased during the elution from an initial 0.01N to 1N.

In elution using hydrochloric acid, preference is given to pumping aqueous hydrochloric acid of different normalities, preferably 0.1-12N HCl and particularly preferably 1-2N HCl, through the cation exchanger loaded with L-cysteine.

Loading, washing step and elution are preferably carried out at 25° C. and the pressure of the surrounding atmosphere, i.e. from 900 to 1100 hPa. However, it can also be carried out at lower or higher temperatures and pressures.

Elution of the L-cysteine using hydrochloric acid gives a purified HCl solution of L-cysteine. This solution can optionally be concentrated and, for example, be decolorized by means of activated carbon. Optionally after addition of HCl, the industrially particularly important product L-cysteine hydrochloride monohydrate is crystallized. The purification by means of double ion exchangers enables L-cysteine to be obtained in high purity, regardless of the composition of the fermentation broth originally applied. Further purification, e.g. by fractional crystallization, is not necessary.

The process of the invention makes it possible to purify L-cysteine effectively, with good yields and economically starting out from an L-cysteine-containing fermentation broth. When it is necessary or desired, any derivatives of L-cysteine, e.g. L-cystine or thiazolidine derivatives, which may be present can, for example, be converted under particular process conditions into L-cysteine so as to increase the yield achieved. Thus, for example, the cleavage of thiazolidine derivatives of cysteine over strongly acidic cation exchangers is known and described in EP 1059288 B1. The cleavage of L-cystine to form L-cysteine by addition of suitable reducing agents is likewise conceivable.

The process described makes it possible, regardless of the composition of the fermentation broth originally applied, to reduce the foreign amino acid content to <5% by weight, preferably <1% by weight, based on L-cysteine. Furthermore, it is also possible to reduce the salt content based on L-cysteine to <10% by weight, preferably <1% by weight. In addition, the process described makes it possible to prepare L-cysteine or L-cysteine hydrochloride or L-cysteine hydrochloride monohydrate in a purity of >98% by weight and an optical purity of >99% from L-cysteine-containing fermentation broths without additional purification, e.g. by fractional crystallization.

Before carrying out the process of the invention, microorganism cells and/or insoluble constituents are preferably separated off from the L-cysteine-containing fermentation broth in a first process step. This is effected, for example, by centrifugation, filtration, decantation, membrane filtration or another method with which a person skilled in the art will be familiar for separating off cells/solids from a fermentation broth. The separation is optionally carried out with addition of a filter aid such as Celite®, activated carbon or diatomaceous earth. In this process step, further insoluble constituents other than the cells, e.g. cystine precipitated from the solution or precipitates of other sparingly soluble constituents as can be formed in the fermentation by the microorganism, are advantageously also separated off from the fermentation broth. Furthermore, macromolecules such as proteins can, for example, be separated off or adsorbed on a filter aid or activated carbon or the like which is optionally used and thus be separated off in this process step. The L-cysteine-containing solution obtained by means of this pretreatment is for the purposes of the present invention also included under the term fermentation broth.

The following examples serve to illustrate the invention.

EXAMPLE 1

Purification of an L-Cysteine-Containing Fermentation Broth by Means of the Process of the Invention 500 ml of cell-free fermentation broth (24 g/l of L-cysteine, 1.2 g/l of L-cystine, 18 g/l of N-acetylserine) were applied with natural pH (pH: 7) to 150 ml of an anion exchange resin (OH⁻ form) commercially available under the name Amberlite® FPA 42Cl from Rohm & Haas. The resin was then washed with 250 ml of water (pH 7) and eluted with 1750 ml of HCl. Here, the acid concentration was increased stepwise every 250 ml, from 0.01M HCl to 0.1M HCl to 0.25M HCl to 0.5M HCl. The cysteine content of the eluate fractions was in each case determined by means of HPLC and the cysteine-containing fractions were combined. Of this combined solution, 500 ml were applied to 120 ml of a cation exchange resin ($H^+$ form), commercially available under the name Amberlite® FPC 14-Na from Rohm & Haas. The resin was then washed with 120 ml of water and eluted with 720 ml of 1M HCl.

The cysteine-containing fractions of the eluate from the anion exchanger contained more than 85% of the L-cysteine present in the fermentation broth applied, and the yield of L-cysteine in the product fractions of the eluate from the cation-exchange resin was quantitative.

EXAMPLE 2

Comparative Example

Purification of an L-cysteine-containing fermentation broth exclusively by means of a cation exchanger (corresponds to the process in EP 1958933 A1), eluent: HCl 6500 ml of a cell-free fermentation broth having a pH of 7 were acidified by means of 6M HCl to pH=1 and centrifuged after 1 hour to separate off denatured proteins and other solids. 5350 ml of the clear, HCl-containing solution (19 g/l of L-cysteine, 1.4 g/l of L-cystine, 8 g/l of N-acetylserine) were purified by means of a cation exchanger (1100 ml of Amberlite® FPC 14-Na, $H^+$ form). The solution was applied to the ion exchanger, the column was washed with 3300 ml of water and eluted with 5500 ml of 1M HCl. The cysteine-containing fractions of the eluate contained 85% of the amount of cysteine used and also cations present in the solution.

EXAMPLE 3

Comparative Example

Purification of an L-cysteine-Containing Fermentation Broth Under Basic Conditions, by Means of a Cation Exchanger, Eluent: $NH_4OH$ 100 ml of a cell-free fermentation broth having a pH of 7 were acidified by means of 6M HCl to pH=1 and centrifuged after 1 hour to separate off denatured proteins and other solids. The clear, HCl-containing solution (20 g/l of L-cysteine, 1.2 g/l of L-cystine, 8 g/l of N-acetylserine) were purified by means of a cation exchanger (20 ml of Amberlite® FPC 14-Na, $H^+$ form). The solution was applied to the ion exchanger, the column was washed with 60 ml of water and eluted with 100 ml of 2M $NH_3$. The product fractions contain about 50% of the L-cysteine present in the fermentation broth applied and also significantly increased amounts of cystine compared to the initial amount.

EXAMPLE 4

Crystallization of L-Cysteine Hydrochloride Monohydrate from the HCl Eluate from Ex. 1

500 ml of a purified L-cysteine-containing solution (eluate obtained using 1M HCl) from example 1 were evaporated at 45° C. and 50 mbar on a rotary evaporator until crystallization commenced, the solution was then slowly brought to room temperature and the temperature was subsequently reduced continuously down to −18° C. After a stirring time of 3 hours, the precipitate was filtered off with suction on a precooled suction filter and dried in air.

Yield: 6.5 g of finely crystalline solid, >98% by weight of cysteine hydrochloride monohydrate (corresponds to a total cysteine yield of 70% based on the starting solution=cell-free fermentation broth)

EXAMPLE 5

Comparative Example

Crystallization of L-cysteine Hydrochloride Monohydrate from the HCl Eluate from Ex. 2

5500 ml of a purified L-cysteine-containing solution (eluate obtained using 1M HCl) from example 2 were evaporated at 45° C. and 50 mbar on a rotary evaporator until crystallization commenced, the solution was then slowly brought to room temperature and the temperature was subsequently reduced continuously down to −18° C. After a stirring time of 3 hours, the precipitate was filtered off with suction on a precooled suction filter and dried in air.

Yield: 120 g of finely crystalline solid, 79% by weight of cysteine hydrochloride monohydrate (corresponds to a total cysteine yield of 64% based on the starting solution=cell-free fermentation broth)

EXAMPLE 6

Comparative Example

Crystallization of L-Cysteine from the $NH_3$ Eluate from Ex. 3

100 ml of a purified L-cysteine-containing solution (eluate obtained using 2M $NH_3$) from example 3 were evaporated at 45° C. and 50 mbar on a rotary evaporator until crystallization commenced, the solution was then slowly brought to room temperature and the temperature was subsequently reduced continuously down to −18° C. After a stirring time of 3 hours, the precipitate was filtered off with suction on a precooled suction filter and dried in air.

Yield: Analysis of the product obtained showed that about 90% of the L-cysteine used were converted into L-cystine under these conditions.

The invention claimed is:
1. A process for purifying L-cysteine from an L-cysteine-containing fermentation broth, comprising:
bringing the L-cysteine-containing fermentation broth into contact at a pH of from 6 to 9 with a basic anion exchanger, wherein the anion exchanger is used in an OH⁻ form such that L-cysteine in the broth binds to the anion exchanger to provide bound L-cysteine, flushing the anion exchanger with a first washing solution, contacting the anion exchanger with an acid to remove the bound L-cysteine from the anion exchanger and to form an eluate containing the L-cysteine, contacting the eluate at a pH of ≤4 with an acidic cation exchanger, such that the L-cysteine binds to the cation exchanger, flushing the cation exchanger with a second washing solution, and contacting the cation exchanger with a strong acid to remove the L-cysteine from the cation exchanger and to provide a purified L-cysteine containing solution.

2. The process as claimed in claim 1, wherein the cation exchanger is strongly acidic and the basic anion exchanger is strongly basic.

3. The process as claimed in claim 1, wherein the anion exchanger is used in a OH⁻ form and the cation exchanger is used in a H⁺ form.

4. The process as claimed in claim 1, wherein the first washing solution is water having a pH in a range from 6 to 8.

5. The process as claimed in claim 1, wherein the second washing solution is water having a pH in a range from 4 to 8.

6. The process as claimed in claim 1, wherein cells and solids are firstly separated off from the fermentation broth.

7. The process as claimed in claim 1, further comprising concentrating the purified L-cysteine-containing solution to provide a concentrated solution and subsequently crystallizing out from the concentrated solution L-cysteine hydrochloride monohydrate.

8. The process as claimed in claim 7, wherein the L-cysteine hydrochloride monohydrate obtained has a purity of >98% by weight.

9. The process as claimed in claim 2, wherein the anion exchanger is used in a OH⁻ form and the cation exchanger is used in a H form.

10. The process as claimed in claim 9, wherein the first washing solution is water having a pH in a range from 6 to 8.

11. The process as claimed in claim 10, wherein the second washing solution is water having a pH in a range from 4 to 8.

12. The process as claimed in claim 11, wherein cells and solids are firstly separated off from the fermentation broth.

13. The process as claimed in claim 12, further comprising concentrating the purified L-cysteine-containing solution to provide a concentrated solution and subsequently crystallizing out from the concentrated solution L-cysteine hydrochloride monohydrate.

14. The process as claimed in claim 13, wherein the L-cysteine hydrochloride monohydrate obtained has a purity of >98% by weight.

* * * * *